(12) United States Patent
Phipps et al.

(10) Patent No.: US 11,406,766 B2
(45) Date of Patent: *Aug. 9, 2022

(54) APPLICATOR SYSTEM AND METHOD FOR FLOWABLE COMPOSITIONS

(71) Applicant: DoseLogix, LLC, Woodstock, GA (US)

(72) Inventors: Timothy Gayle Phipps, Woodstock, GA (US); Dale Melton Coker, Woodstock, GA (US); Daniel Lee DeYoung, Woodstock, GA (US); Ellen Y. Brown, Marietta, GA (US); Saundra D. Naughton, White, GA (US)

(73) Assignee: DOSELOGIX, LLC, Woodstock, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/903,968

(22) Filed: Jun. 17, 2020

(65) Prior Publication Data
US 2020/0316305 A1 Oct. 8, 2020

Related U.S. Application Data

(63) Continuation of application No. 16/031,746, filed on Jul. 10, 2018, now Pat. No. 10,702,654, which is a
(Continued)

(51) Int. Cl.
*A61M 5/315* (2006.01)
*A61M 5/31* (2006.01)
*A61M 5/34* (2006.01)

(52) U.S. Cl.
CPC ...... *A61M 5/31511* (2013.01); *A61M 5/3134* (2013.01); *A61M 5/34* (2013.01);
(Continued)

(58) Field of Classification Search
CPC .. A61M 5/31511; A61M 5/3134; A61M 5/34; A61M 5/345; A61M 2005/3114; A61M 2005/3125
(Continued)

(56) References Cited

U.S. PATENT DOCUMENTS

D19,586 S   1/1890   Smith
D21,197 S   12/1891  Hess et al.
(Continued)

FOREIGN PATENT DOCUMENTS

EP   0858271    3/2000
WO   9716088    5/1997
(Continued)

OTHER PUBLICATIONS

U.S. Appl. No. 16/399,978, Non-Final Office Action dated Aug. 19, 2020, 10 pages.
(Continued)

*Primary Examiner* — Lien M Ngo
(74) *Attorney, Agent, or Firm* — Kilpatrick Townsend & Stockton LLP

(57) ABSTRACT

Described are applicators having a plunger with a plunger body, and a tube having a receptacle end for insertion of the plunger, and a connector end formed of flexible plastic material having a bull-nose shape. As an example, the plunger body can include a viewing window. As another example, the connector end has an internal surface that is free of threaded connectors. The connector end can also have a snap-fit coupling design to couple to a snap-fit nozzle. The snap-fit nozzle can be connected to an adaptor cap or an administering tool of a metering dispenser.

15 Claims, 22 Drawing Sheets

Related U.S. Application Data continuation of application No. 15/172,876, filed on Jun. 3, 2016, now Pat. No. 10,086,146.

(60) Provisional application No. 62/170,512, filed on Jun. 3, 2015.

(52) U.S. Cl.
CPC ..... *A61M 5/345* (2013.01); *A61M 2005/3114* (2013.01); *A61M 2005/3125* (2013.01)

(58) Field of Classification Search
USPC ........ 222/386, 388, 390, 1; 604/11–18, 904, 604/905, 181–186
See application file for complete search history.

(56) References Cited

U.S. PATENT DOCUMENTS

| | | | |
|---|---|---|---|
| 835,446 A | 11/1906 | Lesueur | |
| 1,342,450 A | 6/1920 | Kost et al. | |
| 1,701,663 A | 2/1929 | Clark | |
| D79,445 S | 9/1929 | Solon | |
| D93,591 S | 10/1934 | Wewetzer | |
| D115,881 S | 7/1939 | Lewis | |
| D166,238 S | 3/1952 | Bedinger | |
| D175,832 S | 10/1955 | Gerson | |
| D178,225 S | 7/1956 | Pree | |
| 2,754,822 A * | 7/1956 | Emelock | A61M 31/007 604/59 |
| 2,812,763 A | 11/1957 | Ferguson | |
| 2,869,546 A | 1/1959 | Cantor | |
| 3,026,872 A | 3/1962 | Prater, Jr. | |
| 3,156,387 A | 11/1964 | Harwood | |
| 3,220,413 A * | 11/1965 | Sunnen | A61F 13/26 604/218 |
| 3,227,161 A | 1/1966 | Lorenzo | |
| 3,306,252 A | 2/1967 | Knight et al. | |
| D212,991 S * | 12/1968 | Chister et al. | D24/114 |
| D212,992 S | 12/1968 | Scaler, Jr. | |
| 3,424,158 A | 1/1969 | Silver | |
| 3,540,448 A * | 11/1970 | Sunnenjoseph | A61M 31/00 604/237 |
| 3,581,399 A | 6/1971 | Dragan | |
| 3,656,480 A | 4/1972 | Rubricius | |
| 3,656,482 A * | 4/1972 | Sunnen | B65D 83/28 604/237 |
| 3,910,442 A | 10/1975 | Gargano | |
| D243,430 S | 2/1977 | Thrush | |
| D248,217 S | 6/1978 | Allen et al. | |
| 4,139,127 A | 2/1979 | Gentile | |
| D253,514 S | 11/1979 | Etelson | |
| D255,096 S | 5/1980 | Etelson | |
| 4,298,036 A * | 11/1981 | Horvath | A45D 40/04 141/1 |
| D267,546 S | 1/1983 | Manlove | |
| D270,386 S | 8/1983 | Lee | |
| 4,421,504 A | 12/1983 | Kline | |
| D281,042 S | 10/1985 | Antoni et al. | |
| 4,545,696 A | 10/1985 | Carluccio | |
| D281,350 S | 11/1985 | Heier | |
| 4,645,098 A | 2/1987 | Hoffmann | |
| D300,510 S | 4/1989 | Mason, Jr. | |
| D303,724 S | 9/1989 | Horng et al. | |
| D308,021 S | 5/1990 | Natori | |
| D314,842 S | 2/1991 | Fleming | |
| 5,347,265 A | 9/1994 | Shimura | |
| 5,374,263 A | 12/1994 | Weiler | |
| 5,425,580 A | 6/1995 | Beller | |
| 5,460,782 A | 10/1995 | Coleman et al. | |
| D371,743 S | 7/1996 | Wacker | |
| D373,931 S | 9/1996 | Whitehead | |
| 5,725,133 A | 3/1998 | Iaia | |
| 5,800,169 A * | 9/1998 | Muhlbauer | A61M 5/3129 433/226 |
| 6,027,471 A | 2/2000 | Fallon et al. | |
| 6,234,698 B1 | 5/2001 | De Laforcade | |
| 6,398,763 B1 | 6/2002 | Richardson et al. | |
| 6,474,369 B2 | 11/2002 | Castellano | |
| D501,188 S | 1/2005 | Zhu | |
| 6,981,618 B2 | 1/2006 | Reisinger | |
| D543,456 S | 5/2007 | Muhlemann | |
| 7,213,994 B2 | 5/2007 | Phipps et al. | |
| D557,605 S | 12/2007 | Reber, II et al. | |
| 7,442,179 B1 | 10/2008 | Just | |
| 7,503,905 B2 | 3/2009 | Jessop et al. | |
| D610,678 S | 2/2010 | Kawamura | |
| 8,308,678 B2 | 11/2012 | Swick | |
| D679,195 S | 4/2013 | Markham | |
| D681,459 S | 5/2013 | Ramsey et al. | |
| D688,830 S | 8/2013 | Friedman | |
| 8,544,684 B2 * | 10/2013 | Perez | G01F 13/00 222/39 |
| D693,220 S | 11/2013 | Luo | |
| D710,699 S | 8/2014 | Phelps | |
| 8,801,675 B2 | 8/2014 | Janish et al. | |
| 9,022,258 B2 | 5/2015 | Nehren et al. | |
| D760,077 S | 6/2016 | Rye et al. | |
| D763,096 S | 8/2016 | Jerez Quintana | |
| D772,066 S | 11/2016 | Phipps et al. | |
| D823,116 S | 7/2018 | Phipps et al. | |
| 10,086,146 B2 | 10/2018 | Phipps et al. | |
| 10,308,418 B1 | 6/2019 | Dakolios et al. | |
| 10,322,433 B2 | 6/2019 | Phipps et al. | |
| 10,702,654 B2 | 7/2020 | Phipps et al. | |
| 2002/0049405 A1 * | 4/2002 | Deslauriers | A61B 17/8827 604/82 |
| 2004/0127846 A1 | 7/2004 | Dunn et al. | |
| 2005/0054991 A1 | 3/2005 | Tobyn et al. | |
| 2007/0000946 A1 * | 1/2007 | Phipps | B65D 83/0011 222/129.4 |
| 2007/0078392 A1 * | 4/2007 | Jessop | A61C 5/62 604/122 |
| 2009/0317168 A1 | 12/2009 | Theroude | |
| 2009/0326479 A1 | 12/2009 | Janish et al. | |
| 2009/0326506 A1 | 12/2009 | Hasegawa et al. | |
| 2010/0001026 A1 | 1/2010 | Springhorn et al. | |
| 2012/0035556 A1 | 2/2012 | Nordsiek et al. | |
| 2012/0205393 A1 | 8/2012 | Perez | |
| 2013/0165853 A1 | 6/2013 | Kawamura | |
| 2014/0031323 A1 | 1/2014 | Perez | |
| 2016/0129228 A1 * | 5/2016 | Perez | A61M 31/00 604/60 |
| 2016/0354549 A1 | 12/2016 | Phipps et al. | |
| 2017/0209896 A1 | 7/2017 | Phipps et al. | |
| 2017/0348196 A1 | 12/2017 | Yuki et al. | |
| 2018/0086541 A1 | 3/2018 | Ellsworth et al. | |
| 2020/0148462 A1 | 5/2020 | Brugger et al. | |

FOREIGN PATENT DOCUMENTS

| | | |
|---|---|---|
| WO | 2012131320 | 10/2012 |
| WO | 2016061400 | 4/2016 |

OTHER PUBLICATIONS

U.S. Appl. No. 16/399,978, Notice of Allowance dated Nov. 18, 2020, 5 pages.

Estee Lauder Golden Seashell Compact, Terapeak, Available online at: http://www.terapeak.com/worth/estee-lauder-golden-seashell-compact/191672034924/, Dec. 23, 2015, 3 pages.

Real Seashell Ring Box Take 2, Paul Pape Designs, YouTube, Available online at: https://www.youtube.com/watch?v=389UvZ36X6c, Jun. 9, 2013, 1 page.

U.S. Appl. No. 15/172,876, Final Office Action dated Dec. 4, 2017, 10 pages.

U.S. Appl. No. 15/172,876, Non-Final Office Action dated Mar. 27, 2018, 9 pages.

U.S. Appl. No. 15/172,876, Non-Final Office Action dated Sep. 5, 2017, 9 pages.

U.S. Appl. No. 15/172,876, Notice of Allowance date Jul. 18, 2018, 5 pages.

(56) References Cited

OTHER PUBLICATIONS

U.S. Appl. No. 15/328,401, Non-Final Office Action dated Nov. 16, 2018, 12 pages.
U.S. Appl. No. 15/328,401, Notice of Allowance dated Mar. 6, 2019, 7 pages.
U.S. Appl. No. 15/328,401, Restriction Requirement dated Apr. 11, 2018, 6 pages.
U.S. Appl. No. 16/031,746, Advisory Action dated Sep. 10, 2019, 4 pages.
U.S. Appl. No. 16/031,746, Final Office Action dated Jul. 1, 2019, 11 pages.
U.S. Appl. No. 16/031,746, Non-Final Office Action dated Mar. 19, 2019, 11 pages.
U.S. Appl. No. 16/031,746, Non-Final Office Action dated Oct. 25, 2019, 7 pages.
U.S. Appl. No. 16/031,746, Notice of Allowance dated Feb. 27, 2020, 5 pages.
U.S. Appl. No. 29/529,088, Notice of Allowance dated Jul. 12, 2016, 11 pages.
U.S. Appl. No. 29/582,813, Notice of Allowance dated Mar. 13, 2018, 9 pages.
International Application No. PCT/US2015/055814, International Preliminary Report on Patentability dated Apr. 27, 2017, 20 pages.
International Application No. PCT/US2015/055814, International Search Report and Written Opinion dated Mar. 15, 2016, 28 pages.
International Application No. PCT/US2015/055814, Invitation to Pay Additional Fees and, Where Applicable, Protest Fee dated Jan. 14, 2016, 8 pages.

\* cited by examiner

APPLICATOR SYSTEM AND METHOD FOR FLOWABLE COMPOSITIONS

CROSS-REFERENCE TO RELATED APPLICATIONS

This application is a continuation of U.S. patent application Ser. No. 16/031,746, filed on Jul. 10, 2018 and entitled APPLICATOR SYSTEM AND METHOD FOR FLOWABLE COMPOSITIONS, which is a continuation of U.S. patent application Ser. No. 15/172,876, filed on Jun. 3, 2016 and entitled FLOWABLE COMPOSITION APPLICATOR, now U.S. Pat. No. 10,086,146, which is related to and claims priority benefits from U.S. Provisional Patent Application No. 62/170,512, filed on Jun. 3, 2015 and entitled FLOWABLE COMPOSITION APPLICATOR, all of which are hereby incorporated by reference in their entireties

FIELD OF THE INVENTION

The field of the invention relates to applicators and dispensers for dispensing flowable compositions, and more particularly, to a snap-fit connection for the applicators and/or for the dispensers having a rotatable housing which causes a floor member to rise and urge a predetermined amount of flowable composition through an opening in a cap.

BACKGROUND

Conventionally, applicators for delivering substances to body cavities, such as the vagina and rectum, comprise a blunt, hollow tube or barrel into which a plunger can be inserted. Typically, these tubes are formed of rigid plastic material that has no flexibility during insertion, which often makes use and application difficult and painful for the user.

In many cases, the leading end of the tube includes internal threads to attach the tube to a dispenser for loading the applicator with cream or other flowable substances. When the substance is discharged into the cavity, the threads typically are filled by the substance, resulting in inaccurate dosing. Additionally, this may create hygiene problems for the user because cleaning the tube may not remove all of the substance from the threads and thus bacteria may hide in the threads.

Typically, the user loads the applicator based on markings that appear on the body of the plunger that is positioned inside the tube. If the user does not ensure that the volume of the tube below the plunger is completely filled by the substance (i.e., there are no air gaps inside the tube), then further dosing inaccuracies may occur. Dosing inaccuracies may also occur when loading because the applicator requires the user to squeeze the substance out of the dispenser and into the applicator. In many cases, when the user squeezes the dispenser, the dispenser sucks back some or all of the substance, making it difficult for the user to load the applicator. Thus, loading the applicator requires skill and tedious attention to detail by the user, thereby making it difficult for the user to obtain accurate dosing. Specifically, the user must carefully squeeze the dispenser until the substance reaches the desired marking and then carefully un-thread the applicator from the dispenser to release the vacuum to obtain accurate dosing.

Usually, the user dispenses the substance from the applicator into the body cavity by depressing the plunger into the tube. However, a certain amount of clearance between the plunger and the tube is necessary to avoid leakage of the substance back into the tube. On one hand, if there is too much space between the plunger and the tube, leakage may occur because the substance may remain in the space between the tube and the plunger. On the other hand, if there is not enough space between the plunger and the tube, the plunger may get stuck or bend in the tube, and leakage may result from the substance blowing by the plunger and back into the tube. Consequently, if the clearance is too much or too little, leakage will occur, resulting in inaccurate dosing.

Thus, it may be desirable to provide an applicator with a more flexible/smoother leading end for more comfortable use, a connection design that eliminates the inaccuracies associated with the internal threads in the applicator, as well as a way to improve the dosing accuracy of flowable material into the applicator.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various aspects of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of the present invention, an applicator comprises a plunger having a body, and a tube comprising a receptacle end for insertion of the plunger, and a connector end formed of flexible plastic material having a bull-nose shape.

In certain embodiments, an internal surface of the connector end is free of threaded connectors.

In some embodiments, a viewing window is positioned in the body of the plunger. The plunger body may have a straightness deviation of less than 0.04 inches. The plunger may be manufactured using a mold.

The connector end may comprise a snap-fit coupling design. The snap-fit coupling design may be configured to couple to a snap-fit nozzle comprising a tip positioned proximate a recessed area.

In some embodiments, the snap-fit nozzle is connected to an administering tool. The administering tool may be connected to a metering dispenser.

According to certain embodiments of the present invention, a metering dispenser comprises a body comprising an inner wall, a first end, and a second end, wherein the inner wall defines a chamber having a cross-sectional shape that varies along a longitudinal draft and configured to hold a flowable composition, a drive screw coupled to the second end of the body, wherein the drive screw comprises an elongated shaft having at least one external thread, wherein the elongated shaft is arranged to extend substantially along a length of the chamber, and a plunger comprising a plunger cross-sectional shape, wherein the plunger is positioned within the chamber and is coupled to the elongated shaft of the drive screw so that the plunger travels along the elongated shaft through the chamber when the drive screw is rotated, wherein the plunger comprises at least two annular lips for contact with the inner wall, wherein at least one annular lip of the at least two annular lips is configured to flex in a direction toward the first end of the body so that the plunger forms a fluid seal with the inner wall of the chamber as the plunger travels along the elongated shaft through the chamber.

In some embodiments, the metering dispenser further comprises a base rotationally coupled to the second end of the body, wherein the force required to rotate the base and body relative to each other varies to provide tactile feedback to a user.

In some embodiments, the metering dispenser further comprises a base rotationally coupled to the second end of the body, wherein rotation of the base and body relative to each other provides audible feedback when at least one relative position is reached.

In various embodiments, the metering dispenser may further comprise a child resistant cover. The child resistant cover may be positionable proximate the base to make rotation of the base at least difficult. The child resistant cover may surround the base and require compression at a predetermined position to release the child resistant cover from the base.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

FIGS. 1-22 show certain embodiments of an applicator 1000 according to the present invention for dispensing a flowable composition 20. The flowable composition 20 may include but is not limited to creams or semi-solid emulsions such as oil-in-water creams and water-in-oil creams, gels, sols, colloids, suspensions, solutions, liquids with positive viscosity such as syrups, or other suitable flowable compositions or medicaments.

In certain embodiments, the applicator 1000 may have the following main components: a plunger 1100 and a tube 1200.

In some embodiments, as best illustrated in FIGS. 1-6, 11, 14-17, and 19-21, the plunger 1100 comprises a body 1102 with a flared end 1104 and a tip 1106. In these embodiments, the tube 1200 comprises a hollow core 1202 formed by substantially cylindrical walls 1204 with a receptacle end 1206 and a connector end 1208.

Figure 20:
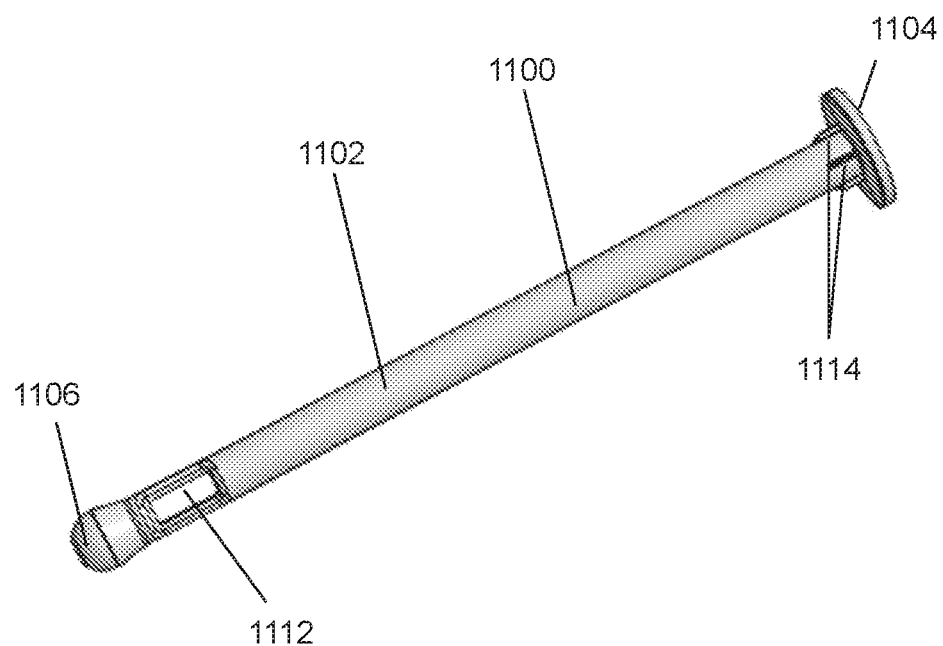
FIG. 20 is a perspective view of the plunger of the applicator of FIG. 19.
Figure 21:
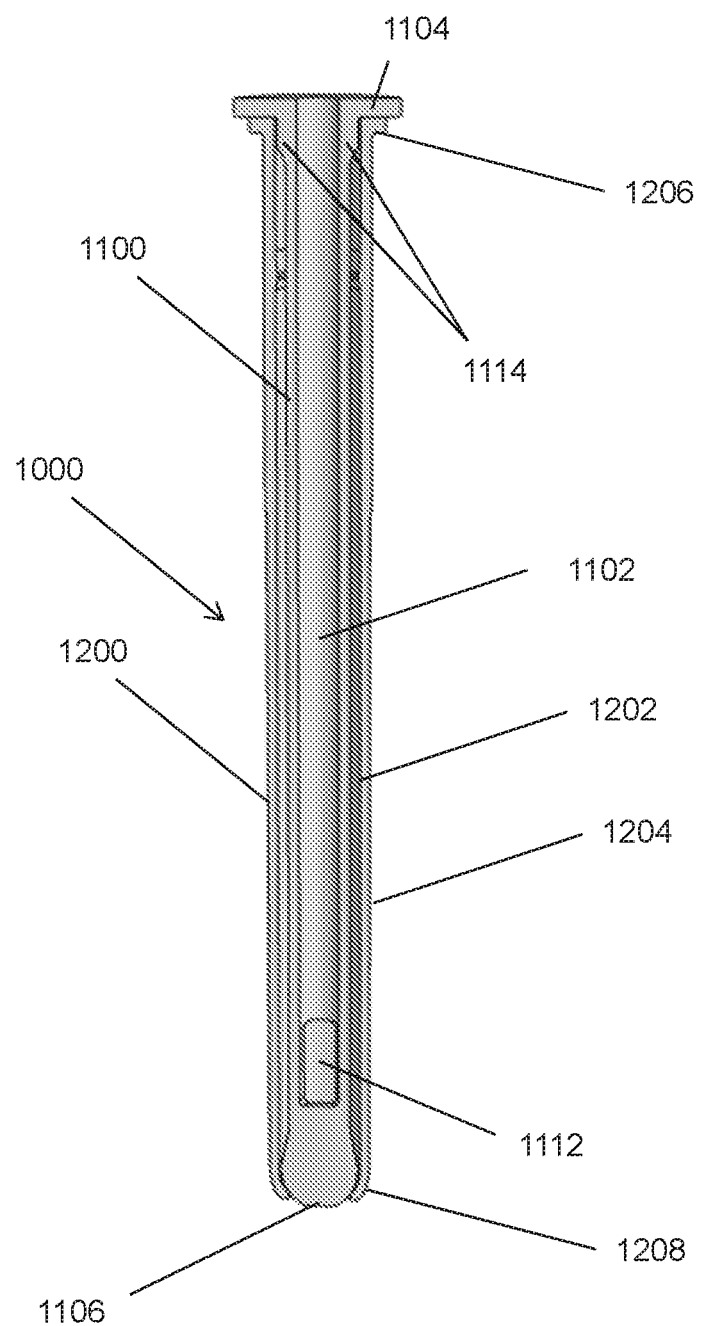
FIG. 21 is a cross-sectional view of the plunger and the tube of the applicator of FIG. 19.
Figure 22:
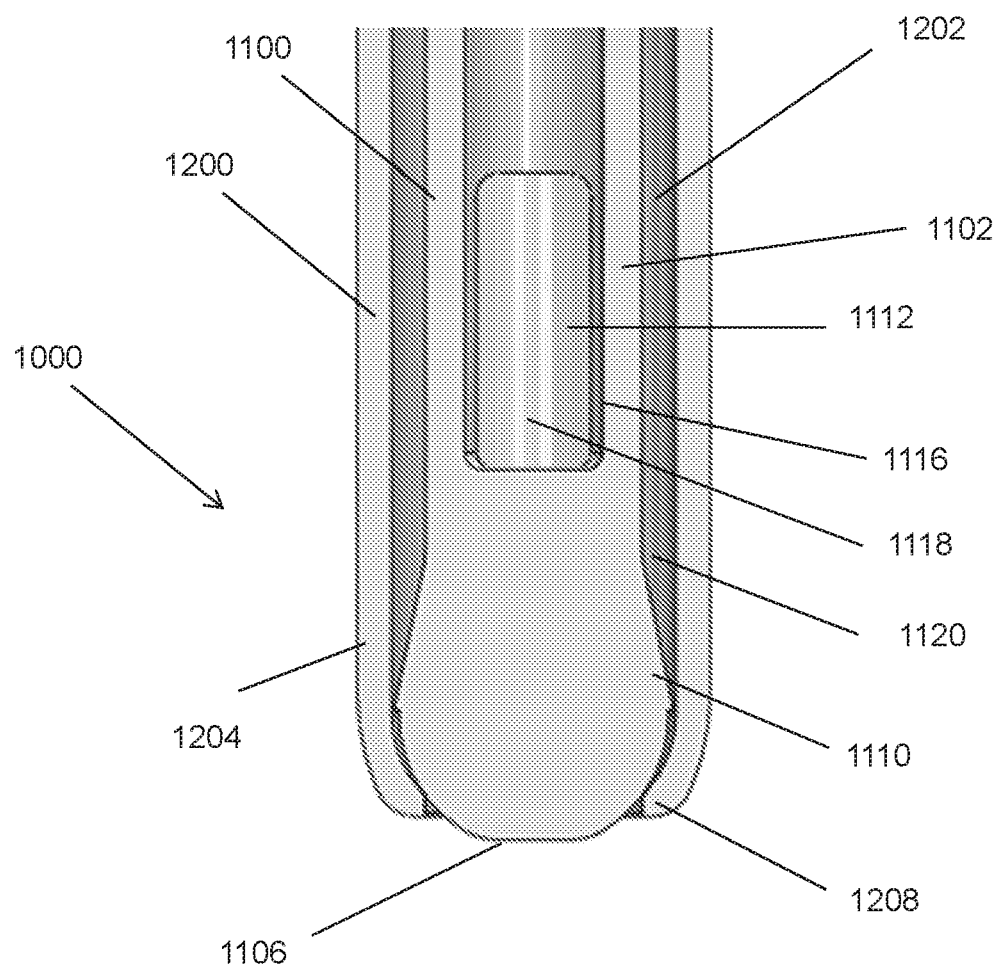
FIG. 22 is a cross-sectional partial view of the plunger and the tube of the applicator of FIG. 19.

In certain embodiments, as best illustrated in FIGS. 20-22, the plunger 1100 may have a viewing window 1112 through the body 1102 of the plunger 1100. The viewing window 1112 is configured to stabilize the plunger 1100 during manufacturing and ensure that the plunger 1100 is manufactured with a substantially straight 1102. For example, with the incorporation of the viewing window 1112, the body 1102 of the plunger 1100 may be manufactured with a straightness tolerance of less than 0.04 inches, which is defined as how much the axis of the body 1102 varies from an ideal straight line. In further embodiments, the straightness tolerance of the plunger body 1100 may be less than 0.02 inches, and the straightness tolerance of the plunger body 1100 may further be less than 0.01 inches.

In certain embodiments, the viewing window 1112 may comprise two strips 1116 of substantially equal thickness and substantially equal length separated by a void 1118. In other embodiments, there may be three or more strips 1116, which are spaced equally or non-equally around the perimeter of the body 1102 so as to form multiple voids 1118.

These strips 1116 are shaped with sufficient thickness and length to ensure that the plunger body 1102 remains substantially rigid when the plunger 1100 is in use.

The improved straightness of the plunger 1100 provided by the viewing window 1112 allows less leakage of flowable composition 20 during dispension. The improved stability of the plunger 1100 also allows the plunger 1100 to be manufactured using a mold while also achieving a straightness tolerance of less than 0.04 inches, and more specifically of less than 0.02 inches, and even more specifically, of less than 0.01 inches. Additionally, the viewing window 1112 facilitates cleaning of the plunger 1100, as a cleaning solution may be poured through the viewing window 1112.

In certain embodiments, the plunger 1100 may include a set of marks 1108 along a side of the body 1102, with each mark correlating to a particular quantity of flowable composition 20 remaining in the tube 1200. In these embodiments, the walls 1204 of the tube 1200, or at least a portion thereof, is preferably clear or translucent so that the marks 1108 may be viewed through the tube 1200. In other embodiments, it is not necessary to view the marks 1108 through the tube 1200, as the mark is designed to indicate the volume inside the tube 1200 when the desired mark 1108 is aligned with an edge of the receptacle end 1206 of the tube 1200. In further embodiments, the plunger 1100 may not include any marks.

The tip 1106 of the plunger 1100, in some embodiments, may be rounded, which provides additional comfort for the user. The tip 1106 may also be formed of a mesh material, which further enhances comfort for the user. When the plunger 1100 is inserted into the tube 1200, the tip 1106 is inserted through the receptacle end of the tube 1200 and the hollow core 1202 until the tip 1106 reaches the connector end 1208 of the tube 1200, at which point the flared end 1104 of the plunger 1100 is positioned against the receptacle end 1206 of the tube 1200.

In some embodiments, as best illustrated in FIGS. 20-22, the plunger 1100 may include ribs 1114 by the flared end 1104 that are configured to guide the plunger 1100 through the tube 1200 in a substantially straight direction. The ribs 1114 may be tapered, having their widest portion closest to the flared end 1104 of the plunger 1100. The improved guidance of the plunger 1100 by the ribs 1114 in a substantially straight direction prevents leakage of the flowable composition 20, which allows better dispension of the flowable composition 20 than was possible with conventional applicators 1000.

In certain embodiments, the tip 1106 of the plunger 1100 may include a lip 1110 that is configured to form a fluid seal with the cylindrical walls 1204 of the tube 1200. In particular, the lip 1110 may be an annular ring having a flexible design configured to flexibly bend, compress, flex, and/or expand as needed to allow the plunger 1100 to maintain a fluid seal with the walls 1204 of the tube 1200. The improved fluid seal with the lip 1110 allows less viscous materials 20 to be dispensed with the applicator 1000 than was possible with conventional applicators 1000. The improved fluid seal with the lip 1110 also prevents more flowable material 20 from recessing back into the applicator 1000 than was possible with conventional applicators.

Figure 1:
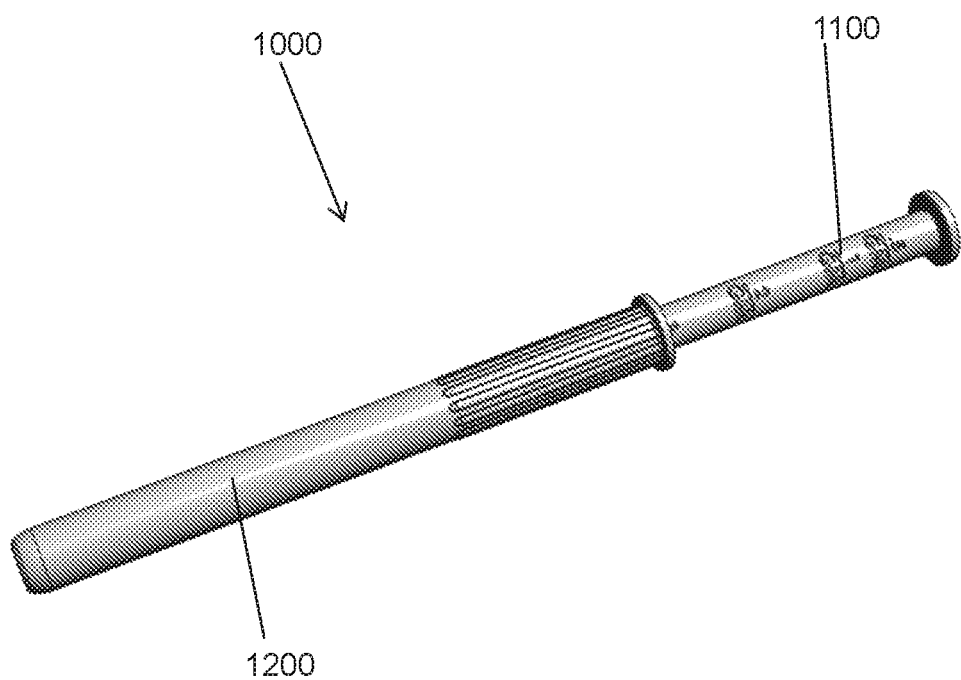
FIG. 1 is a perspective view of an applicator, according to certain embodiments of the present invention.
Figure 2:
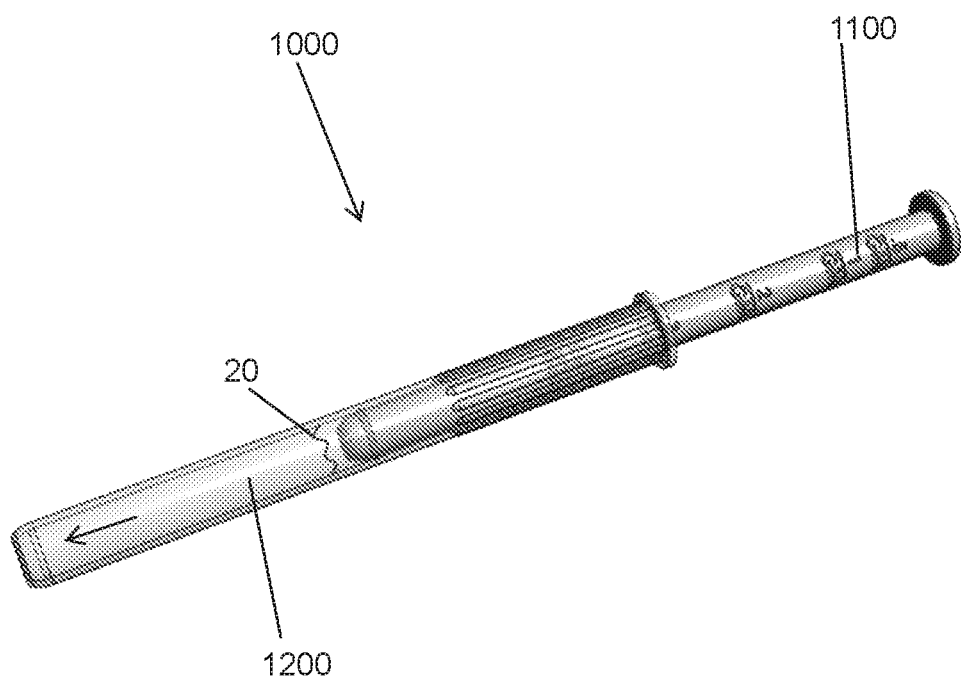
FIG. 2 is a perspective view of the applicator of FIG. 1 with the tube shown as transparent to view the plunger positioned therein.
Figure 3:
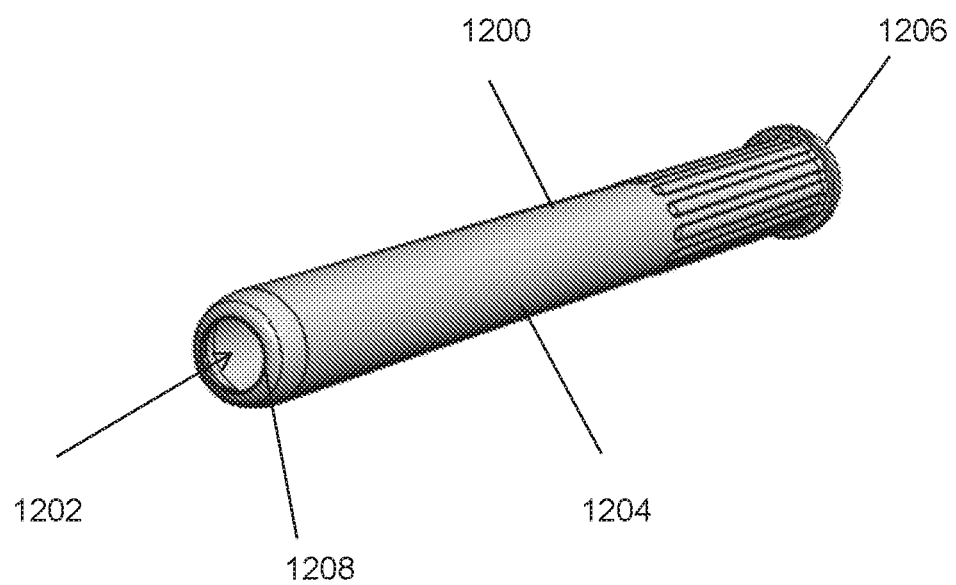
FIG. 3 is a perspective view of the tube of the applicator of FIG. 1, as viewed from the connector end.
Figure 4:
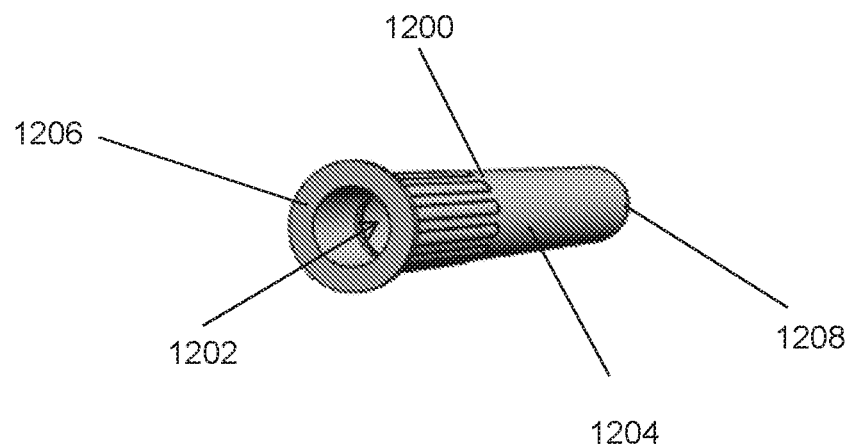
FIG. 4 is a perspective view of the tube of the applicator of FIG. 1, as viewed from the receptacle end.
Figure 5:
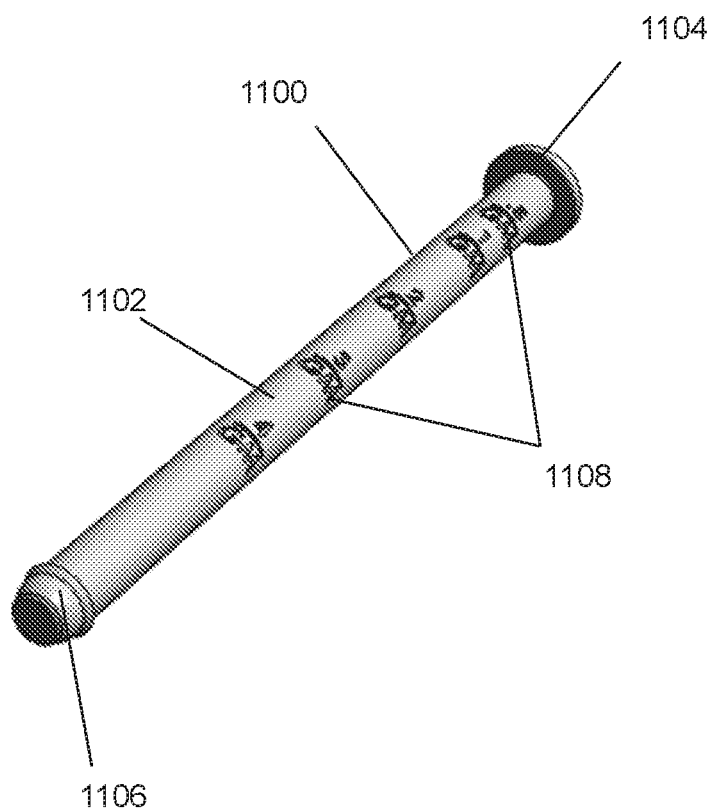
FIG. 5 is a perspective view of the plunger of the applicator of FIG. 1.
Figure 6:
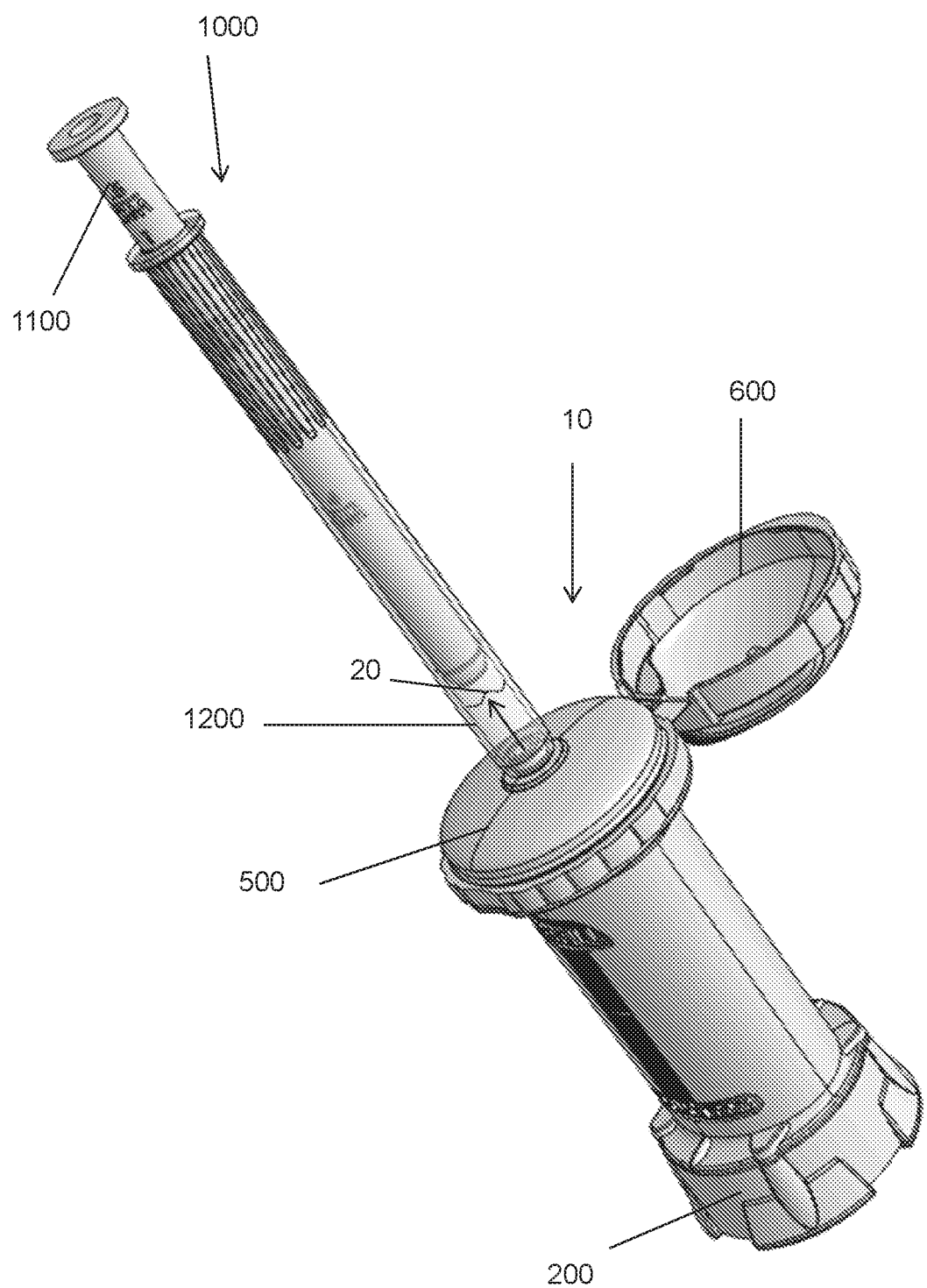
FIG. 6 is a perspective view of the applicator of FIG. 1 connected to a snap-fit nozzle of an administering tool of a dispenser, according to certain embodiments of the present invention.
Figure 7:
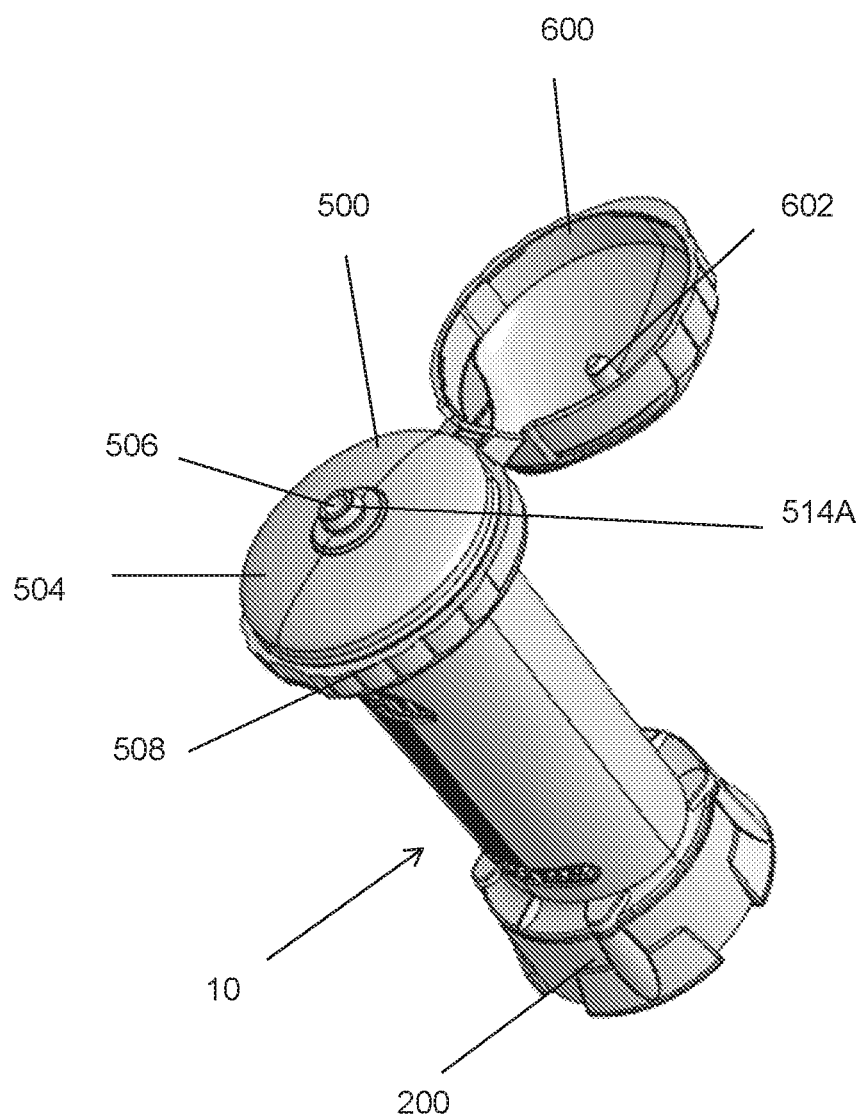
FIG. 7 is a perspective view of the snap-fit nozzle of the administering tool and the dispenser of FIG. 6.
Figure 8:
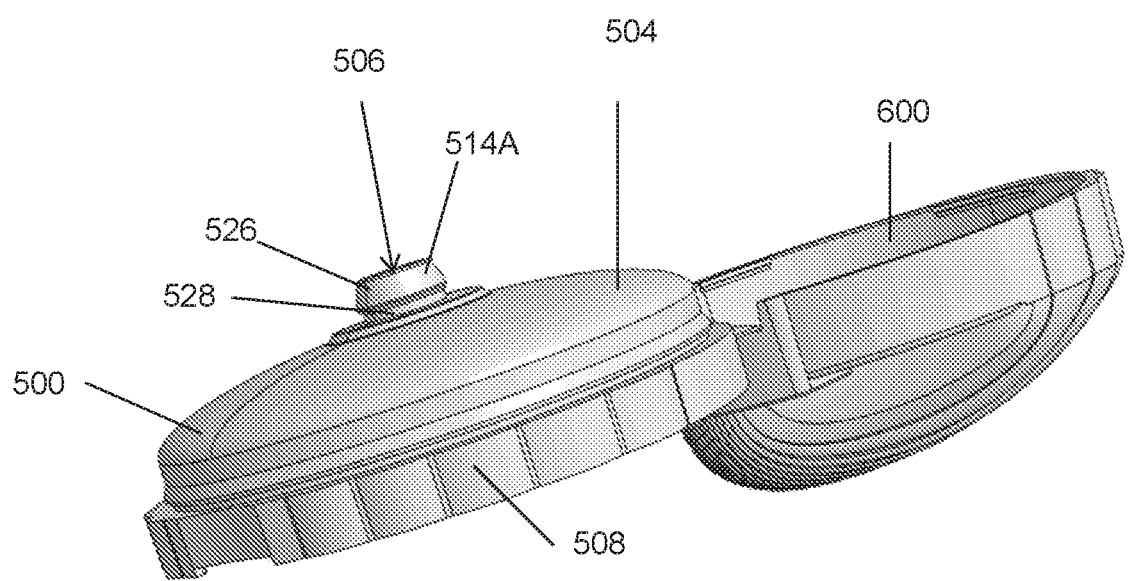
FIG. 8 is a side perspective view of the snap-fit nozzle of the administering tool of FIG. 6.
Figure 9:
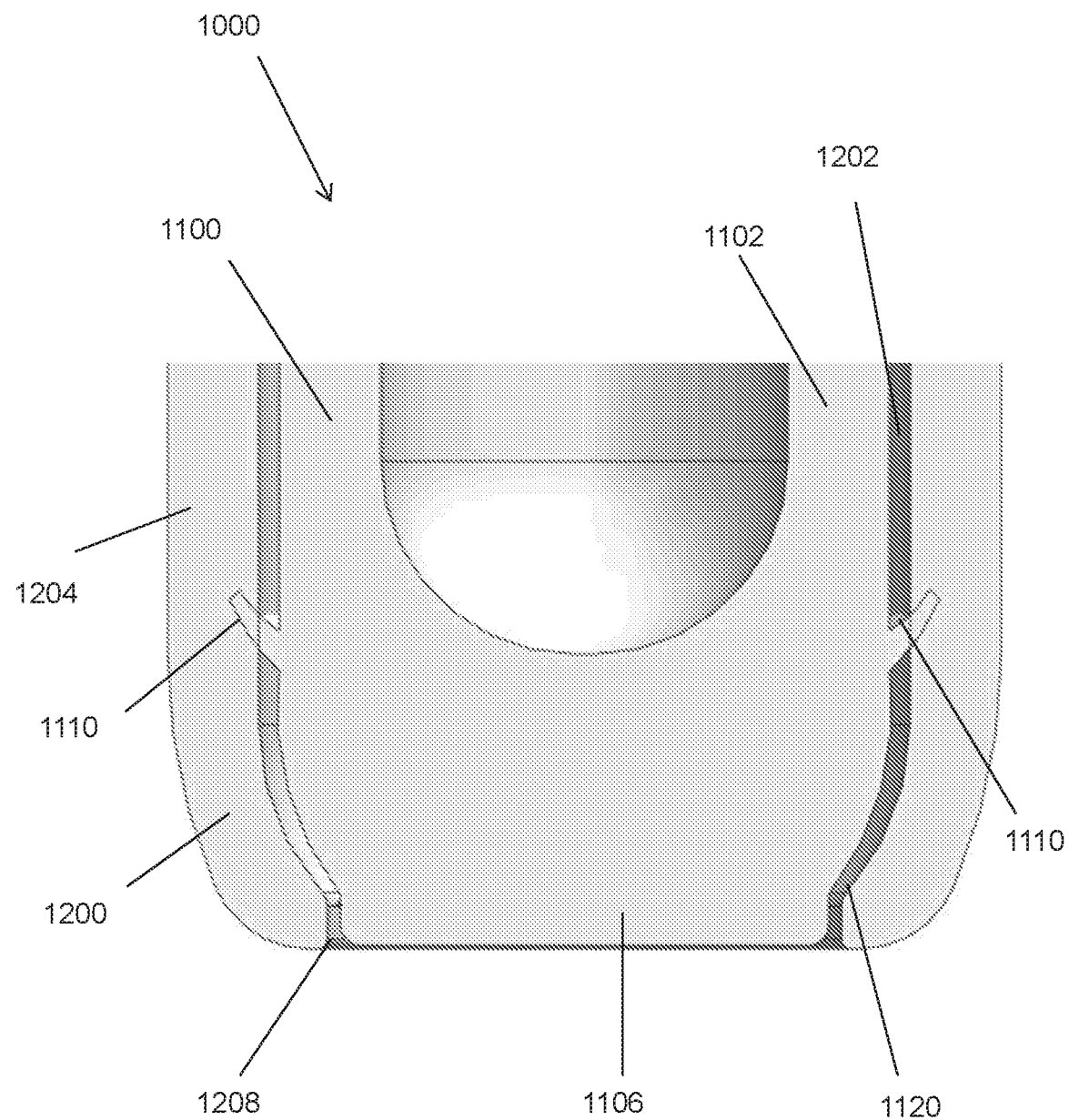
FIG. 9 is a cross-sectional partial view of the plunger and the tube of the applicator of FIG. 1 with the plunger positioned adjacent the connector end.

As best illustrated in FIGS. 9-10 and 21-22, when the plunger 1100 is inserted into the tube 1200, a gap 1120 is formed between the plunger 1100 and the walls 1204 of the hollow core 1202 of the tube 1200. In certain embodiments, as illustrated by FIG. 9, the width of the gap 1120 is relatively constant along the body 1102, such that the gap 1120 is closed by the annular ring design of the lip 1110. In other words, the tip 1106 diameter does not expand beyond the diameter of the body 1102.

In other embodiments, as best illustrated in FIG. 22, the tip 1106 diameter increases toward the lip 1110 such that the gap 1120 is partially narrowed by the tip 1106 configuration, with the remaining gap 1120 being closed by the lip 1110. In these embodiments, the flared shape of the tip 1106 assists the lip 1110 to maintain firm contact with the cylindrical walls 1204 by minimizing the distance between the widest point on tip 1106 and the cylindrical walls 1204.

Figure 10:
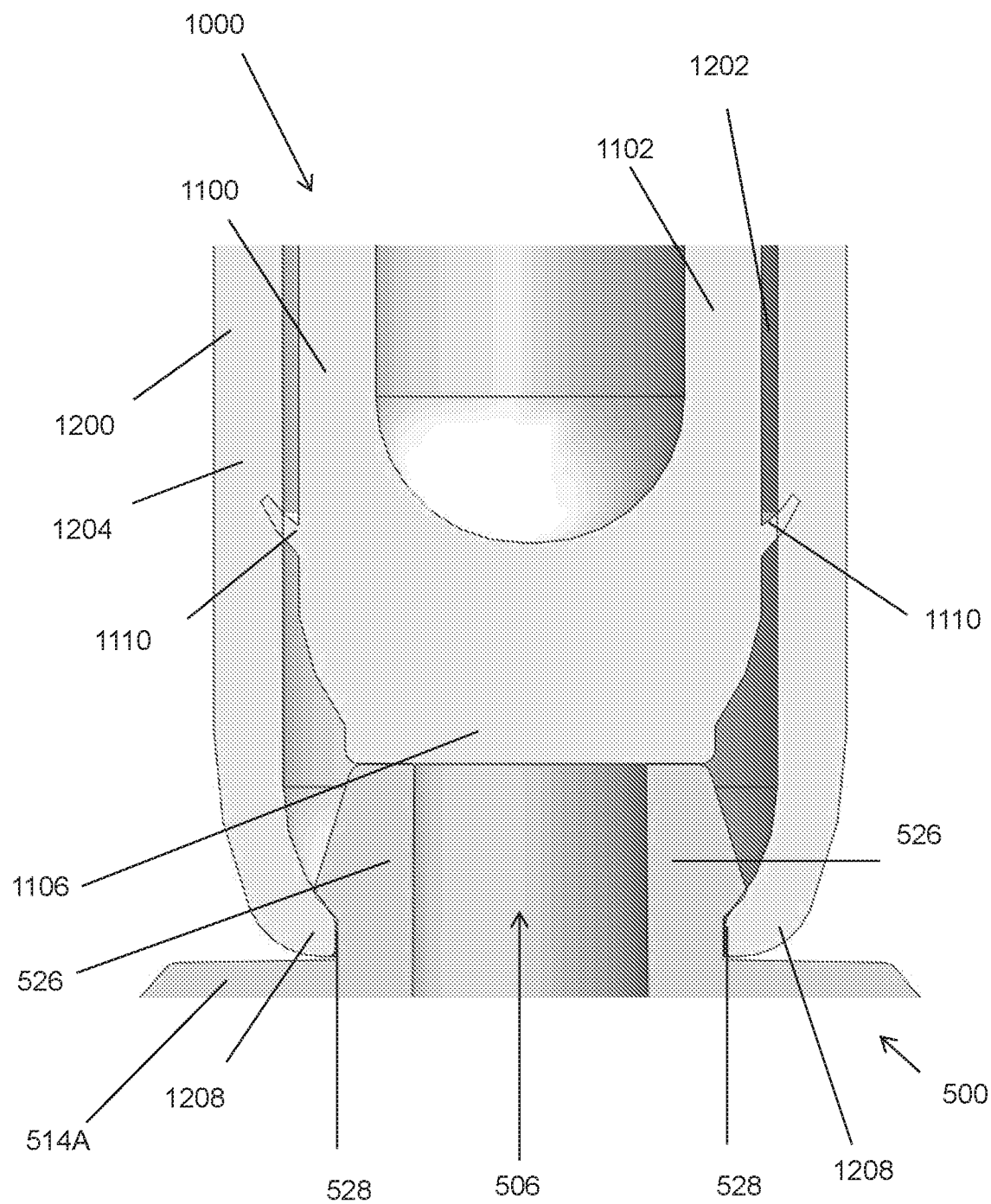
FIG. 10 is a cross-sectional partial view of the plunger and the tube of the applicator of FIG. 1 connected to the snap-fit nozzle of the administering tool of FIG. 6 with the plunger positioned adjacent the snap-fit nozzle.
Figure 11:
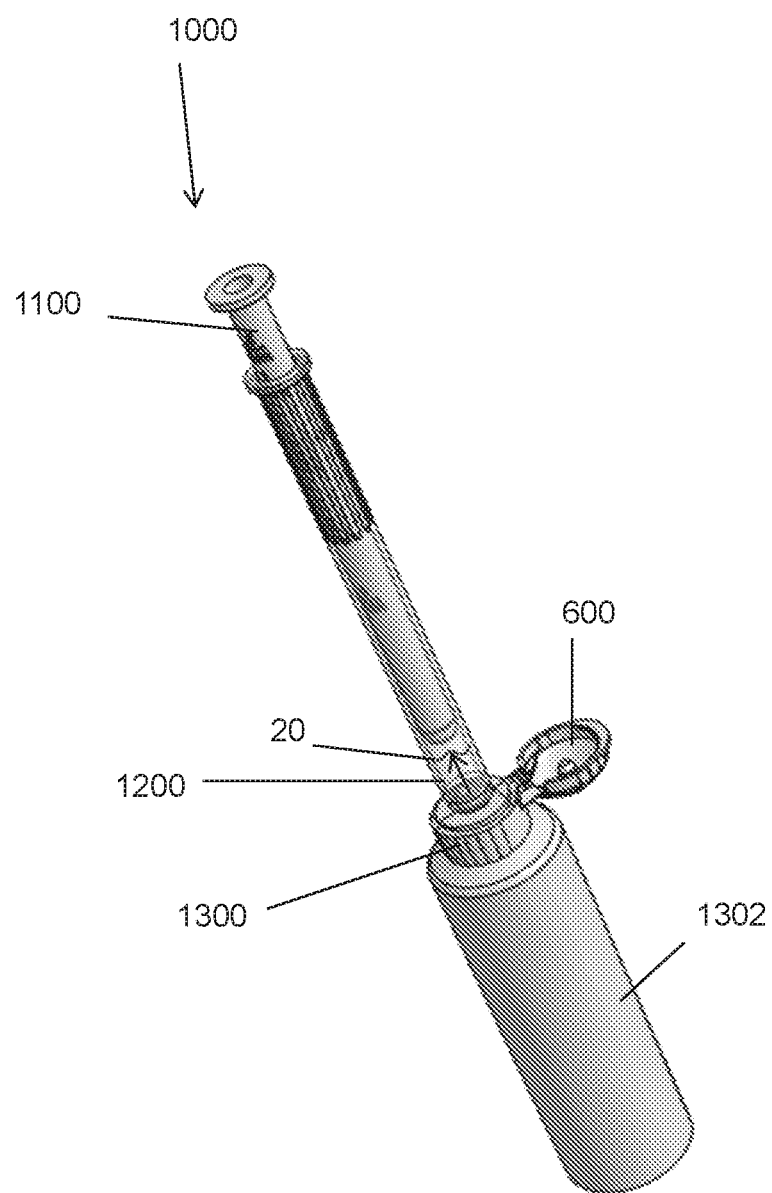
FIG. 11 is a perspective view of the administering tool of FIG. 1 connected to a snap-fit nozzle of an adaptor cap connected to an off-the-shelf or prescription threaded tube, according to certain embodiments of the present invention.
Figure 12:
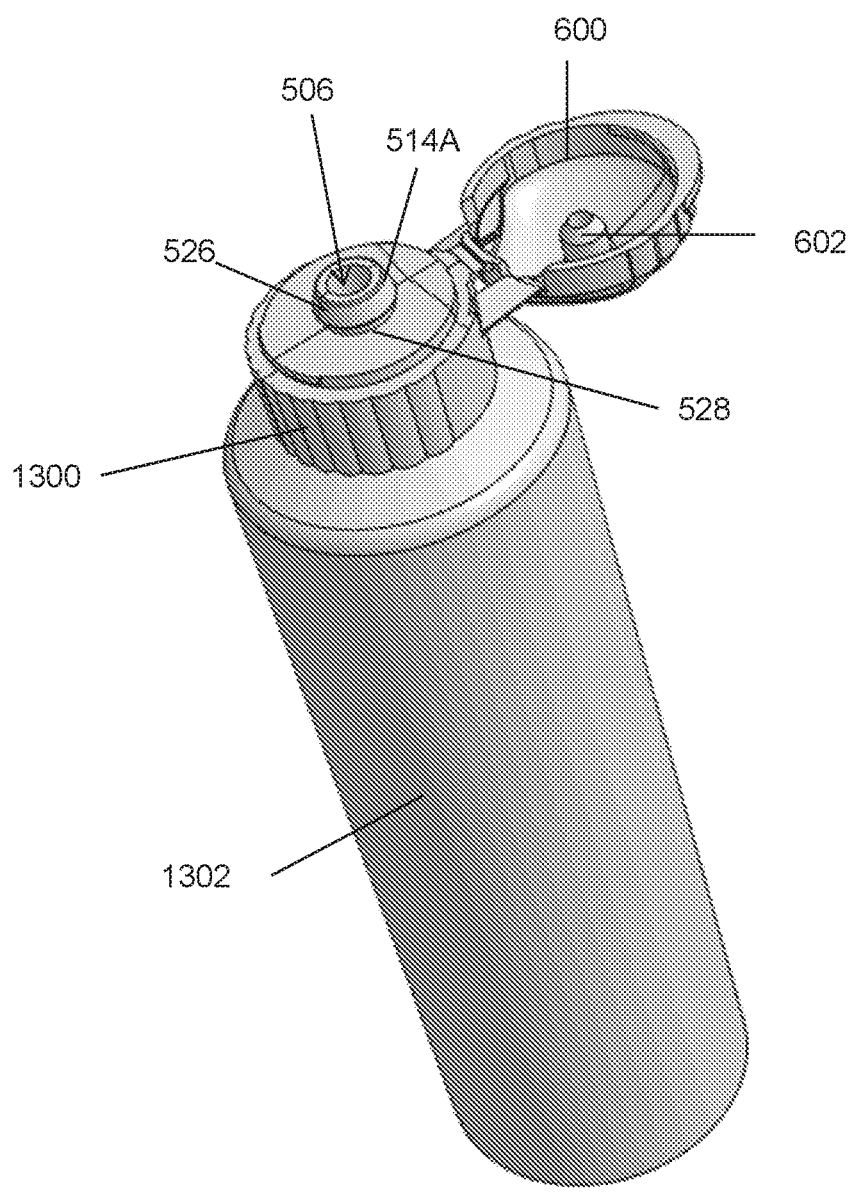
FIG. 12 is a perspective view of the snap-fit nozzle of the adaptor cap and the tube of FIG. 11.
Figure 13:
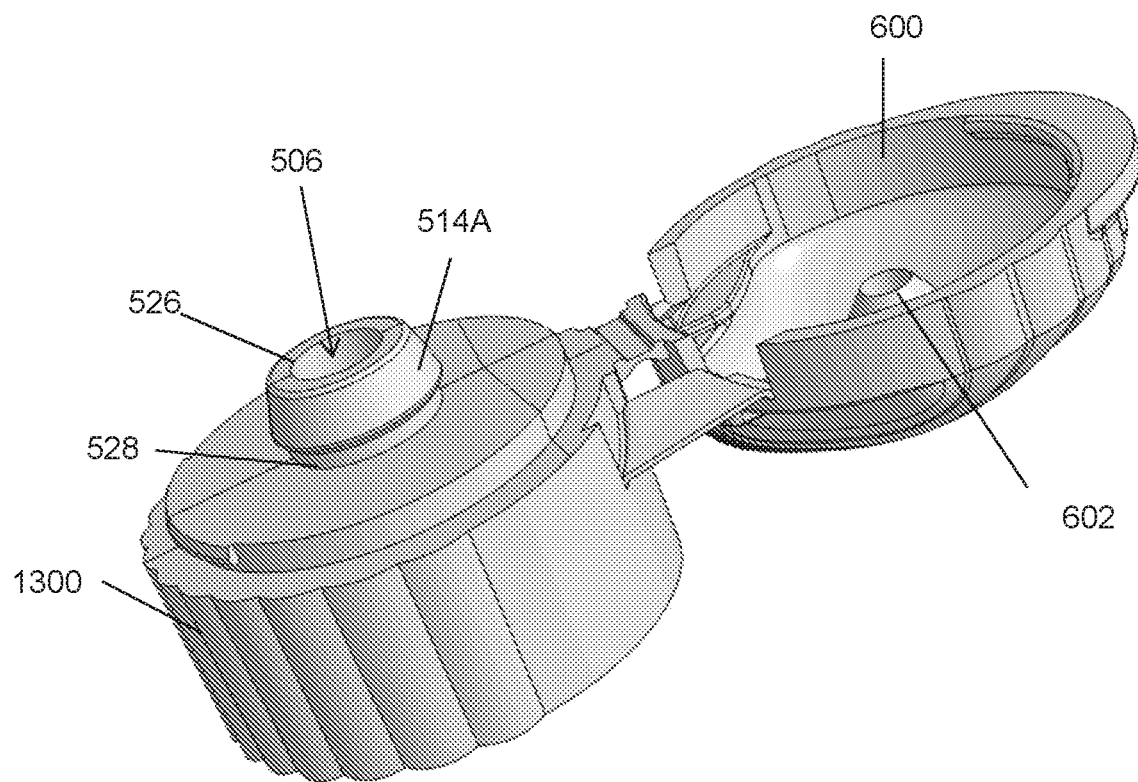
FIG. 13 is a side perspective view of the snap-fit nozzle of the adaptor cap of FIG. 11.
Figure 14:
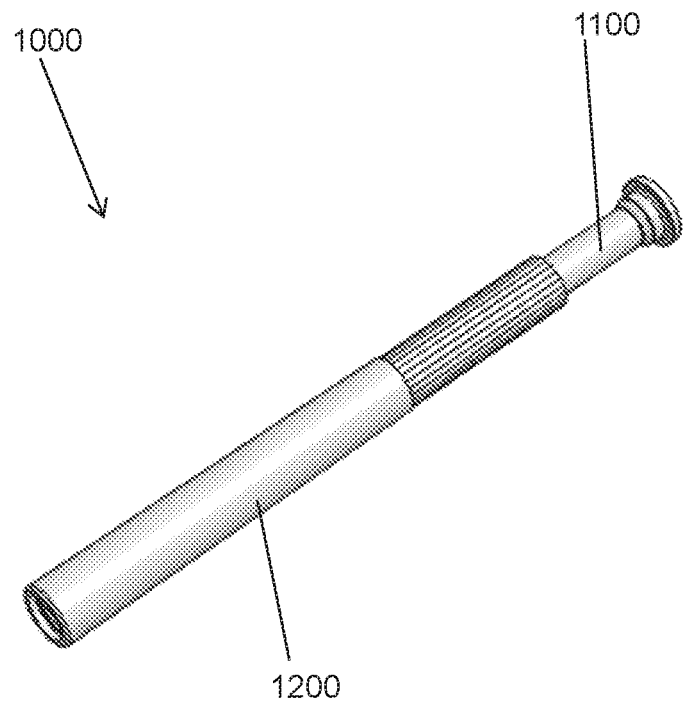
FIG. 14 is a perspective view of an applicator, according to certain embodiments of the present invention.
Figure 15:
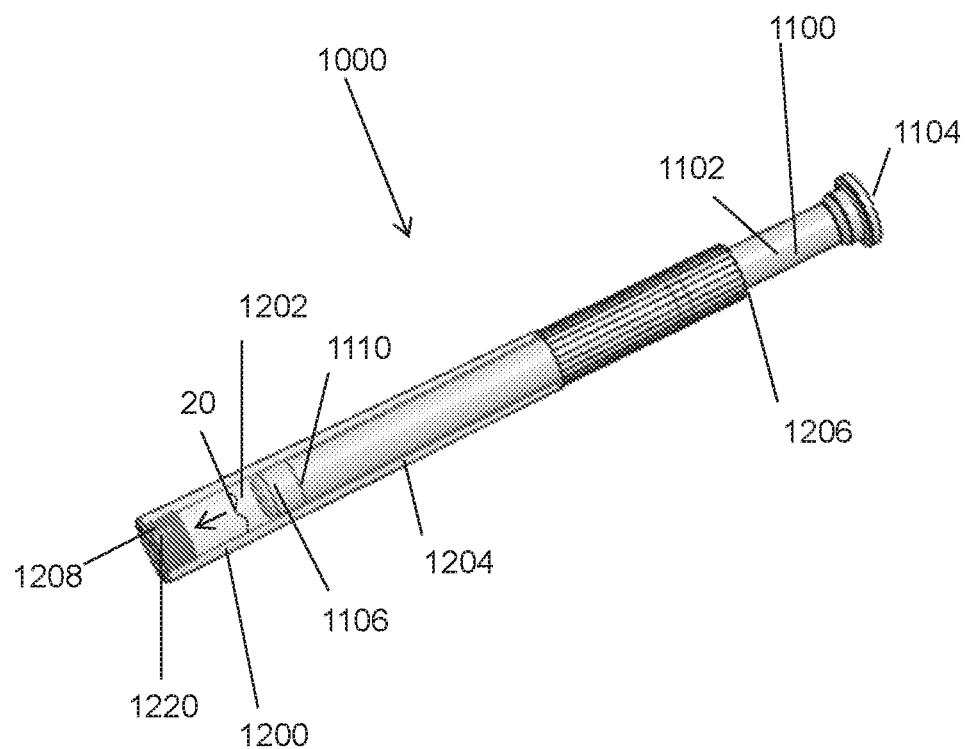
FIG. 15 is a perspective view of the applicator of FIG. 14 with the tube shown as transparent to view the plunger positioned therein.
Figure 16:
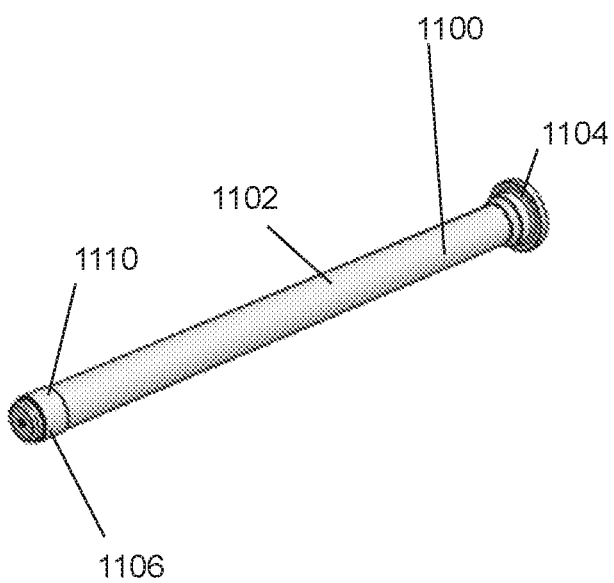
FIG. 16 is a perspective view of the plunger of the applicator of FIG. 14.
Figure 17:
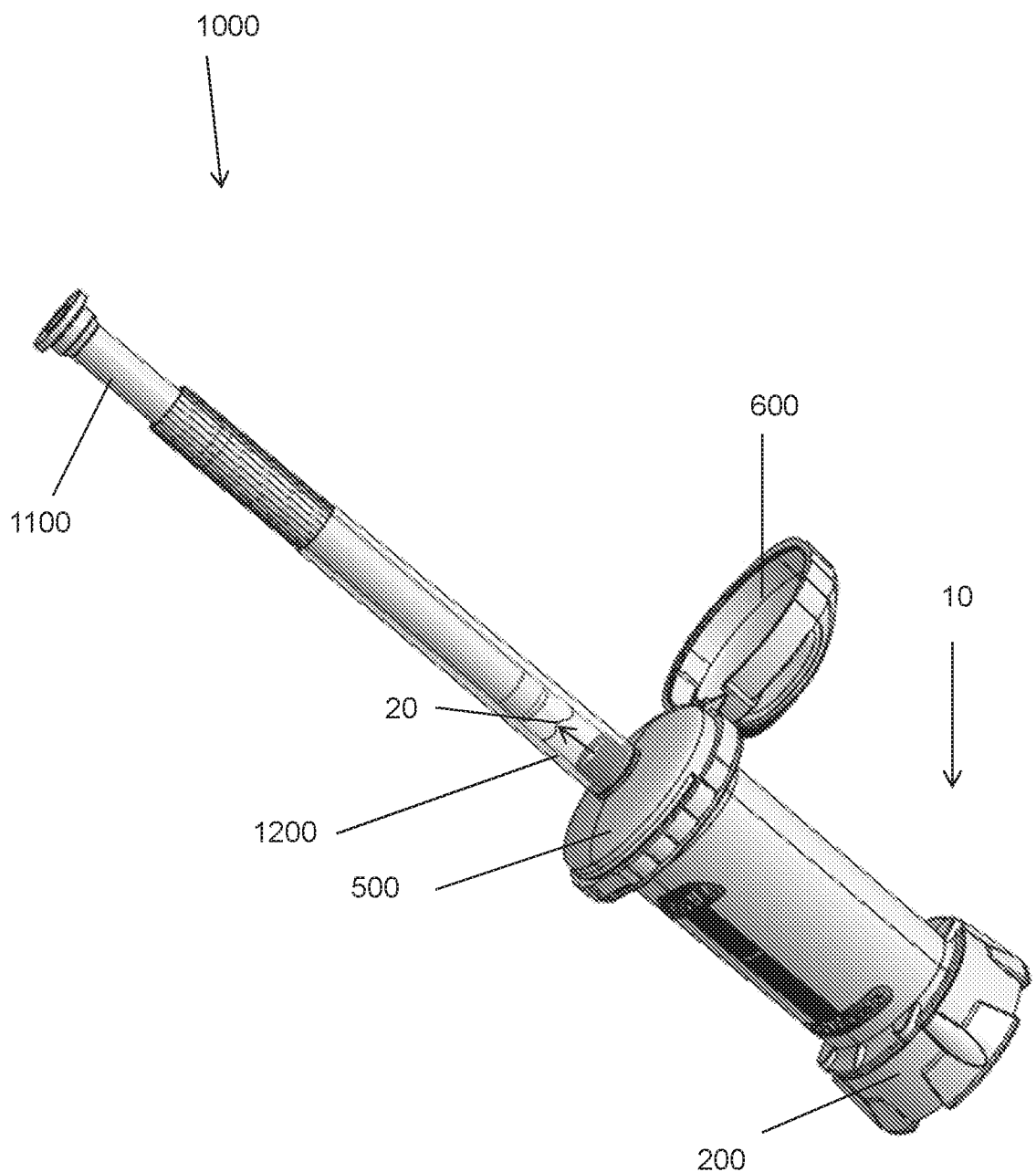
FIG. 17 is a perspective view of the applicator of FIG. 14 connected to a threaded nozzle of an administering tool of a dispenser, according to certain embodiments of the present invention.
Figure 18:
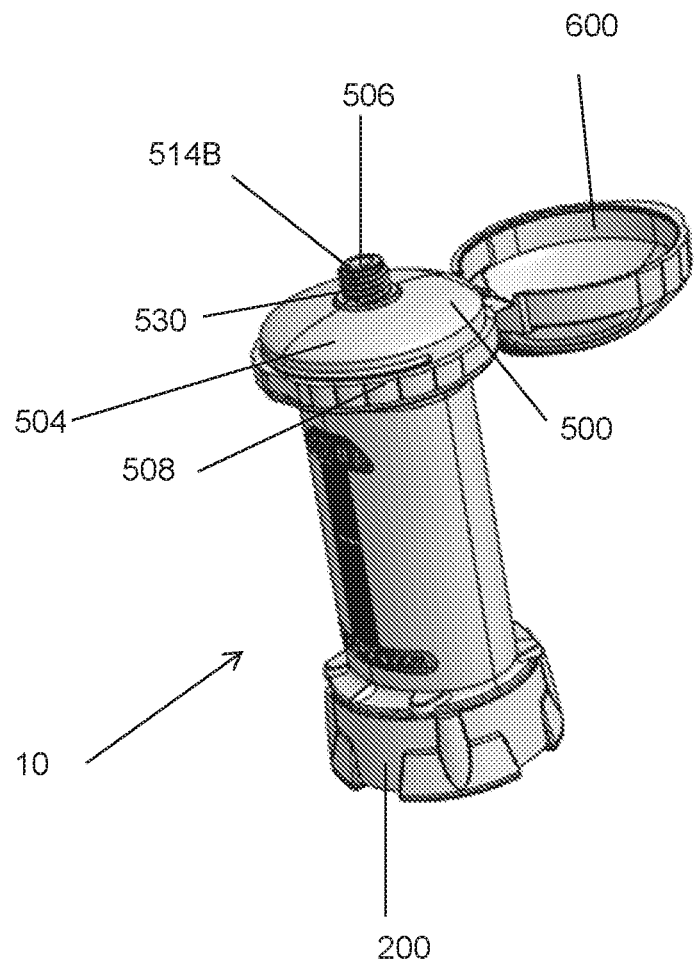
FIG. 18 is a perspective view of the threaded nozzle of the administering tool and the dispenser of FIG. 17.
Figure 19:
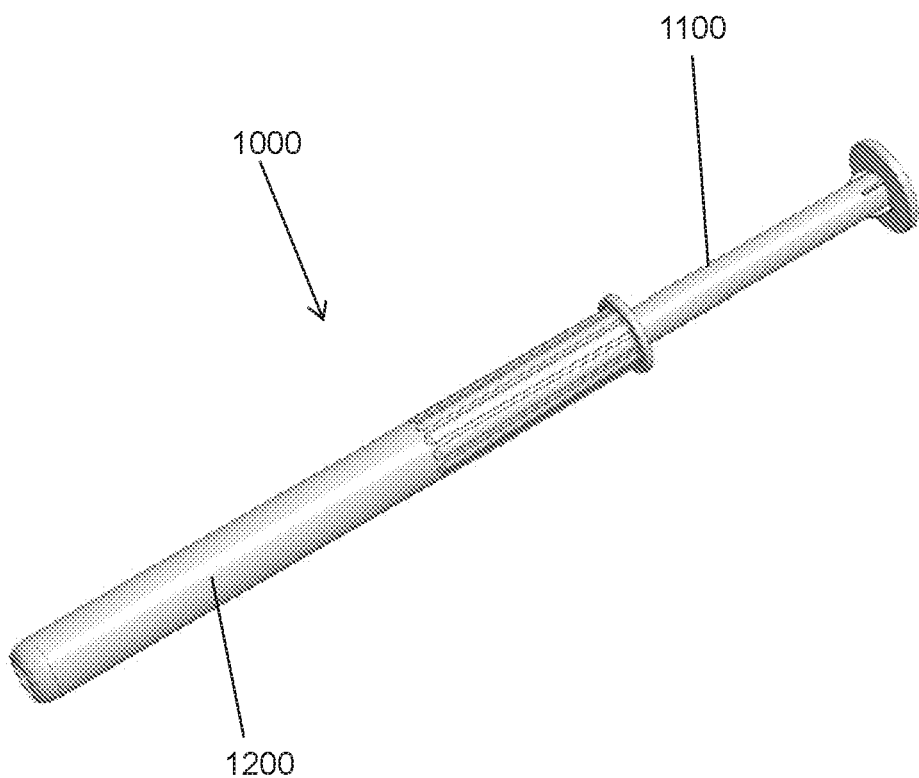
FIG. 19 is a perspective view of an applicator, according to certain embodiments of the present invention.

As best illustrated in FIGS. 9-10, the tip 1106 and the connector end 1208 may comprise complementary mating shapes that are free from threaded internal connectors, which prevents residual flowable composition 20 from being trapped between the plunger 1100 and the tube 1200 when the plunger 1100 is fully depressed into the tube 1200.

In some embodiments, as best illustrated in FIGS. 21 and 22, the tip 1106 protrudes at least a portion beyond the connector end 1208 of the tube when the plunger 1100 is fully depressed into the tube 1200, which prevents any recess of flowable composition 20 after dispension. This protrusion also facilitates cleaning of the tip 1106 of the plunger 1100.

To fill the applicator 1000 with flowable composition 20, the applicator 1000 may be connected to a dispenser for loading the applicator 1000 with flowable composition 20, as illustrated in FIGS. 6-8, 10-13, and 17-18. In certain embodiments, the administering tool 500 may be designed to work with the dispenser 10 described in U.S. Provisional Application No. 62/064,259, filed Oct. 15, 2014, entitled "Metering Dispenser for Flowable Compositions," ("the '259 application"), the entire contents of which is incorporated herein by reference. In these embodiments, the administering tool 500 may comprise a curved or domed top surface 504 having at least one hole 506 therein and a sidewall 508. In certain embodiments, a nozzle 514 may be used in place of the at least one hole 506 and/or may be an extension thereof.

In certain embodiments, a cap 600 may be configured as a flip-top design that snaps over the administering tool 500, and which is sized to fit snugly over the administering tool 500 to prevent contamination and to reduce evaporation of the flowable composition 20.

The cap 600 may have downward projecting protrusions 602 which are receivable within the hole 506 of the administering tool 500. The protrusions 602 substantially seal the hole 506 when the cap 600 is in place, thereby reducing the risk of contamination of the flowable composition 20 and preventing clogging of the hole 506. Preferably, the cap 600 has a registering means to align with the administering tool 500 to make alignment of the protrusion 602 and the hole 506 easier.

The dispenser nozzle 514 may be configured to couple to the connector end 1208 of the application via a variety of connection designs.

In certain embodiments, as best illustrated in FIGS. 1-10, the connector end 1208 may be designed to connect to a snap-fit nozzle 514A. In these embodiments, the snap-fit nozzle 514A comprises a tip 526 and a recessed area 528 located below the tip 526. The tip 526 may be configured to have a tapered shape with a narrower end that expands until it reaches the recessed area 528. The connector end 1208 may comprise a flexible opening that expands around the tip 526 as it is inserted into the connector end 1208 until the connector end 1208 reaches the recessed area 528. At that point, recessed area 528 is shaped to allow the connector end 1208 to substantially return to its unstretched size. The connector end 1208 is then retained and held in place by the geometry of the tip 526 and the recessed area 528. As a result, the applicator 1000 is held in an upright position by the snap-fit nozzle 514A.

Once the applicator 1000 has been connected to the snap-fit nozzle 514A, a user turns the base 200 of the dispenser 10 to advance the flowable composition 20 from the dispenser 10 into the applicator 1000. As described in detail in the '259 application, rotation of the base 200 to each home or "click" position delivers a specific amount of flowable composition 20.

After the appropriate amount of flowable composition 20 has been dispensed into the applicator 1000 through the rotation of the base 200 through an appropriate number of home or "click" positions, a user pulls the applicator 1000 upwards until the connector end 1208 expands back over the tip 526 to disconnect the applicator 1000 from the dispenser 10. The user then dispenses the medicine by depressing the plunger 1100 to dispense the flowable composition 20 back through the connector end 1208.

In these embodiments, use of a flexible snap-fit design for the connector end 1208 allows the connector end 1208 to be formed of a soft pliable plastic, which provides a more comfortable insertion and application than conventional applicators, such as those with threaded connections. The bull-nosed shape of the connector end 1208 adds to the comfort of the design. Furthermore, the use of the snap-fit design over conventional threaded connections allows the applicator 1000 to have approximately 80% less residual volume due to the absence of threaded connections in the connector end 1208.

In further embodiments, as illustrated in FIGS. 9-13, the connector end 1208 may be designed to connect to a snap-fit nozzle 514A that is attached to an adaptor cap 1300. The nozzle 514A may comprise the same snap-fit features described above, including a cap 600 with protrusions 602, while the administering tool 500 is otherwise replaced by the adaptor cap 1300. The adaptor cap 1300 is designed to couple to off-the-shelf or prescription threaded tubes 1302 containing the flowable composition 20. In these embodiments, the patient has the benefit of the improved comfort and reduced residual volume in the applicator 1000, but is able to use a conventional source for the flowable composition 20.

In these embodiments, the user connects the applicator 1000 to the snap-fit nozzle 514A as described above. The user then dispenses the flowable composition 20 into the applicator 1000 by squeezing the tube 1302. In these embodiments, the appropriate amount of flowable composition 20 to be dispensed is determined by gauging when the appropriate marking 1108 is aligned with the edge of the receptacle end 1206 of the tube 1200.

The user then disconnects the applicator 1000 from the snap-fit nozzle 514 as described above. The user then dispenses the medicine by depressing the plunger 1100 to dispense the flowable composition 20 back through the connector end 1208.

In further embodiments, as illustrated in FIGS. 14-18, the nozzle 514 may be a threaded nozzle 514B having threads 530, and the connector end 1208 may comprise complimentary threads 1210 for connecting the applicator 1000 to the dispenser 10. In these embodiments, the threaded connection allows users to benefit from the accuracy of the dispenser 10, while still using a conventional connection design. To load the applicator 1000, a user screws a threaded version of the connector end 1208 onto the threaded nozzle 514B, and turns the base 200 of the dispenser 10 to advance the flowable composition 20 from the dispenser 10 into the applicator 1000 until the appropriate amount of flowable composition 20 has been dispensed into the applicator 1000. The user then unscrews the connector end 1208 from the threaded nozzle 514B, and dispenses the medicine by depressing the plunger 1100 to dispense the flowable composition 20 back through the connector end 1208.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. A method of dispensing a flowable composition comprising:
   positioning a plunger of an applicator within a tube of the applicator such that a tip of the plunger is in a dispensed position;
   positioning a dispenser nozzle of an administering tool relative to the applicator and moving the tip of the plunger from the dispensed position to a loaded position; and
   loading the flowable composition into the tube of the applicator from the administering tool after the tip of the plunger is in the loaded position, wherein loading the flowable composition comprises moving the tip of the plunger from the loaded position to a filled position, wherein a distance between the tip of the plunger and a connector end of the tube in the loaded position is greater than a distance between the tip of the plunger and the connector end of the tube in the dispensed position and less than a distance between the tip of the plunger and the connector end of the tube in the filled position.

2. The method of claim 1, wherein moving the tip of the plunger from the dispensed position to the loaded position comprises positioning a portion of the dispenser nozzle within the tube of the applicator such that the dispenser nozzle moves the plunger from the dispensed position to the loaded position.

3. The method of claim 1, further comprising:
   detaching the dispenser nozzle from the applicator after loading the flowable composition; and
   dispensing the flowable composition from the applicator, wherein dispensing the flowable composition comprises moving the plunger within the tube of the applicator such that the tip of the plunger is moved from the filled position to the dispensed position.

4. The method of claim 3, wherein the tip of the plunger protrudes a predetermined distance through the connector end of the tube and away from the connector end of the tube when the plunger is in the dispensed position.

5. The method of claim 1, wherein the administering tool comprises a metering dispenser, and wherein loading the flowable composition into the applicator comprises loading a predetermined amount of the flowable composition into the applicator.

6. The method of claim 1, wherein the administering tool comprising a metering dispenser, and wherein positioning the dispenser nozzle relative to the applicator comprises positioning the metering dispenser relative to the applicator.

7. The method of claim 6, wherein the metering dispenser comprises:
   a body comprising an inner wall, a first end, and a second end, wherein the inner wall defines a chamber configured to hold the flowable composition;
   an elongated shaft; and
   a plunger coupled to the shaft such that rotation of the elongated shaft positions the plunger within the chamber,
   wherein loading the flowable composition into the tube of the applicator comprises rotating the elongated shaft such that the plunger is advanced within the chamber.

8. The method of claim 6, wherein the metering dispenser comprises:
   a body comprising an inner wall, a first end, and a second end, wherein the inner wall defines a chamber configured to hold the flowable composition; and
   a base rotatably coupled to the second end of the body,
   wherein loading the flowable composition into the tube of the applicator comprises rotating the base relative to the body such that the rotation of the base relative to the body provides tactile feedback.

9. A method of dispensing a flowable composition comprising:
   positioning a plunger of an applicator within a tube of the applicator, wherein the tube comprises a receptacle end and a connector end, wherein the plunger comprises a tip, and wherein at least the tip of the plunger is positioned within the tube;
   positioning a dispenser nozzle of a metering device relative to the applicator and with the tip of the plunger within the tube and between the receptacle end and the connector end, wherein the metering device comprises:
   a body comprising an inner wall, a first end, and a second end, wherein the inner wall defines a chamber configured to hold the flowable composition;
   an elongated shaft; and
   a plunger coupled to the shaft such that rotation of the elongated shaft positions the plunger within the chamber; and
   loading the flowable composition into the tube of the applicator from the metering dispenser with the tip of the plunger between the receptacle end and the connector end, wherein loading the flowable composition comprises moving the tip within the tube such that a distance between the tip and the connector end is increased, and wherein loading the flowable composition into the tube of the applicator comprises rotating the elongated shaft such that the plunger is advanced within the chamber.

10. The method of claim 9, wherein the metering device further comprises a base rotatably coupled to the second end of the body, and wherein loading the flowable composition into the tube of the applicator comprises rotating the base relative to the body such that the rotation of the base relative to the body provides tactile feedback.

11. The method of claim 9, wherein positioning the dispenser nozzle of the metering device comprises positioning a portion of the dispenser nozzle within the tube such that a nozzle tip of the dispenser nozzle abuts the tip of the plunger within the tub prior to loading of the flowable composition.

12. The method of claim 9, wherein the metering device further comprises a rotatable base coupled to the second end of the body, wherein loading the flowable composition into the tube of the applicator comprises rotating the rotatable base relative to the body such that the flowable composition is advance through the dispenser nozzle.

13. The method of claim 12, wherein the rotatable base defines a plurality of predefined rotation positions to a predetermined amount of flowable composition, and wherein loading the flowable composition comprises rotating the rotatable base to at least one of the predefined rotation positions such that the predetermined amount of flowable composition is advanced through the dispenser nozzle.

14. A method of dispensing a flowable composition comprising:
   positioning a plunger of an applicator within a tube of the applicator;
   positioning a dispenser nozzle of a metering device relative to the applicator and with a tip of the plunger recessed within the tube between a connector end and a receptacle end of the tube, wherein the metering device comprises the dispenser nozzle, a dispenser body configured to house the flowable composition, and a rotatable base configured to advance the flowable composition through the dispenser nozzle based on rotation of the rotatable base; and
   loading the flowable composition into the tube of the applicator from the a metering device after the tip of the plunger is recessed within the tube between the connector end and the receptacle end of the tube, wherein loading the flowable composition comprises moving the tip of the plunger and reducing a distance between the tip of the plunger and the receptacle end of the tube, and wherein loading the flowable composition comprises rotating the rotatable base relative to the dispenser body such that the flowable composition is advance through the dispenser nozzle.

15. The method of claim 14, wherein the rotatable base defines a plurality of predefined rotation positions to a predetermined amount of flowable composition, and wherein loading the flowable composition comprises rotating the rotatable base to at least one of the predefined rotation positions such that the predetermined amount of flowable composition is advanced through the dispenser nozzle.

* * * * *